United States Patent
Chen et al.

(10) Patent No.: US 8,507,406 B2
(45) Date of Patent: Aug. 13, 2013

(54) ZN4(OH)2(1,2,4-BTC)2—A ROD PACKING MICROPOROUS METAL-ORGANIC FRAMEWORK WITH OPEN METAL SITES FOR SELECTIVE SEPARATION AND SENSING OF SMALL MOLECULES

(75) Inventors: Banglin Chen, San Antonio, TX (US); Zhangjing Zhang, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 187 days.

(21) Appl. No.: 13/136,868

(22) Filed: Aug. 12, 2011

(65) Prior Publication Data
US 2012/0040471 A1    Feb. 16, 2012

Related U.S. Application Data

(60) Provisional application No. 61/401,392, filed on Aug. 12, 2010.

(51) Int. Cl.
*B01J 20/22* (2006.01)

(52) U.S. Cl.
USPC ............. 502/401; 502/424; 95/90; 95/141; 95/143; 95/144; 95/147; 423/247; 423/248; 436/172

(58) Field of Classification Search
None
See application file for complete search history.

(56) References Cited

U.S. PATENT DOCUMENTS

| | | | |
|---|---|---|---|
| 2007/0248852 A1 | 10/2007 | Mueller et al. | 95/90 |
| 2007/0252641 A1 | 11/2007 | Goodnow et al. | 327/543 |

FOREIGN PATENT DOCUMENTS

| | | |
|---|---|---|
| JP | 2003-342260 | 12/2003 |
| JP | 2004-161675 | 6/2004 |
| JP | 2004-305985 | 11/2004 |
| WO | WO 2008/000694 | 1/2008 |

OTHER PUBLICATIONS

Banerjee, et al., "Control of pore size and functionality in isoreticular zeolitic imidazolate frameworks and their carbon dioxide selective capture properties," *J. Am. Chem. Soc.*, 131:3875-7, 2009.

Bauer, et al, "Influence of connectivity and porosity on ligand-based luminescence in zinc metal—organic framework," *J. Am. Chem. Soc.*, 129:7136-44, 2007.

Bourrelly, et al., "Different adsorption behaviors of methane and carbon dioxide in the isotypic nanoporous metal terephthalates MIL-53 and MIL-47," *J. Am. Chem. Soc.*, 127:13519-21, 2005.

Britt, et al, "Highly efficient separation of carbon dioxide by a metal-organic framework replete with open metal sites," *PNAS*, 106:20637-40, 2009.

Chandler, et al., "Microporous metal-organic frameworks formed in a stepwise manner from luminescent building blocks," *J. Am. Chem. Soc.*, 128:10403-12, 2006.

Chen, et al., "A luminescent microporous metal-organic framework for the recognition and sensing of anions," *J. Am. Chem. Soc.*, 6718-9, 2008.

Chen, et al., "A triply interpenetrated microporous metal-organic framework for selective sorption of gas molecules," *Inorg. Chem.*, 46:8490-2, 2007.

(Continued)

*Primary Examiner* — Robert Xu
(74) *Attorney, Agent, or Firm* — Parker Highlander PLLC

(57) ABSTRACT

Disclosed herein are rod-packing robust microporous metal-organic frameworks having the repeat unit $Zn_4(OH)_2(1,2,4-BTC)_2$, useful for applications such as selective gas storage, selective gas sorption and/or separation, selective sensing of chemicals, and catalysis.

21 Claims, 15 Drawing Sheets

(56) References Cited

OTHER PUBLICATIONS

Chen, et al., "High H2 adsorption in a microporous metal-organic framework with open metal sites," *Angew. Chem. Int. Ed. Engl.*, 44:4745-9, 2005.
Chen, et al., "Luminescent open metal sites within a metal-organic framework for sensing small molecules," *Adv. Mater.*, 19:1693-6, 2007.
Chen, et al., "Metal-organic frameworks with functional pores for recognition of small molecules," *Acc. Chem. Res.*, 43:1115-24, 2010.
Chen, et al., "Multiroute synthesis of porous anionic frameworks and size-tunable extraframework organic cation-controlled gas sorption properties," *J. Am. Chem. Soc.*, 131:16027-9, 2009.
Chen, et al., "Rationally designed micropores within a metal-organic framework for selective sorption of gas molecules," *Inorg. Chem.*, 46:1233-6, 2007.
Chen, et al., "Selective gas sorption within a dynamic metal-organic framework," *Inorg. Chem.*, 46:9705-9, 2007.
Chen, et al., "Surface interactions and quantum kinetic molecular sieving for H2 and D2 adsorption on a mixed metal-organic framework material," *J. Am. Chem. Soc.*, 130:6411-23, 2008.
Choi and Suh, "Highly selective $CO_2$ capture in flexible 3D coordination polymer networks," *Angew. Chem.*, 121:6997-7001, 2009.
Chui, et al., "A chemically functionalizable nanoporous material," *Science*, 283:1148-50, 1999.
Dietzel, et al., "Adsorption properties and structure of $CO_2$ adsorbed on open coordination sites of metal-organic framework $Ni_2(dhtp)$ from gas adsorption, IR spectroscopy and X-ray diffraction," *Chem. Commun.*, pp. 5125-5127, 2008.
Dietzel, et al., "An in situ high-temperature single-crystal investigation of a dehydrated metal-organic framework compound and field-induced magnetization of one-dimensional metal-oxygen chains," *Angew. Chem. Int. Ed.*, 44:6354-8, 2005.
Dietzel, et al., "Hydrogen adsorption in a nickel based coordination polymer with open metal sites in the cylindrical cavities of the desolvated framework," *Chem. Commun.*, 959-61, 2006.
Dietzel, et al., "Structural changes and coordinatively unsaturated metal atoms on dehydration of honeycomb analogous microporous metal-organic frameworks," *Chemistry*, 14:2389-97, 2008.
Dincă and Long, "Hydrogen storage in microporous metal-organic frameworks with exposed metal sites," *Angew. Chem. Int. Ed. Engl.*, 47:6766-79, 2008.
Dybtsev, et al., "A homochiral metal-organic material with permanent porosity, enantioselective sorption properties, and catalytic activity," *Angew. Chem. Int. Ed.*, 45:916-920, 2006.
Eddaoudi, et al., "Modular chemistry: secondary building units as a basis for the design of highly porous and robust metal-organic carboxylate frameworks," *Acc. Chem. Res.*, 34:319-30, 2001.
Eddaoudi, et al., "Systematic design of pore size and functionality in isoreticular MOFs and their application in methane storage," *Science*, 295:469-72, 2002.
Fang, et al., "A metal-organic framework with the zeolite MTN topology containing large cages of vol. 2.5 $nm^3$" *Angew. Chem. Int. Ed.*, 44:3845-8, 2005.
Fang, et al., "Mesoporous metal-organic framework with rare etb topology for hydrogen strorage and dye assembly," *Angew. Chem.*, 119:6758-62, 2007.
Férey, "Hybrid porous solids: past, present, future," *Chem. Soc. Rev.*, 37:191-214, 2008.
Hermes, et al., "Selective nucleation and growth of metal-organic open framework thin films on patterned COOH/CF3-terminated self-assembled monolayers on Au(111)," *J. Am. Chem. Soc.*, 127:13744-5, 2005.
Hou, et al., "Porous metal-organic framework based on mu4-oxo tetrazinc clusters: sorption and guest-dependent luminescent properties," *Inorg. Chem.*, 47:1346-51, 2008.
Hu, et al., "A new MOF-505 analog exhibiting high acetylene storage," *Chem. Commun.*, pp. 7551-3, 2009.

Huang, et al., "Shape-selective sorption and fluorescent sensing of aromatics in a flexible network of tetrakis[(4-methylthiophenyl)ethynyl]silane and $AgBF_4$," *Chem. Mater.*, 21:541-6, 2009.
Hwang, et al., "Amine grafting on coordinatively unsaturated metal centers of MOFs: consequences for catalysis and metal encapsulation," *Angew. Chem. Int. Ed.*, 47:4144-8, 2008.
International Search Report and Written Opinion, issued in PCT/US2010/023773, dated Apr. 1, 2010.
Kesanli, et al., "Highly interpenetrated metal-organic frameworks for hydrogen storage," *Angew. Chem. Int. Ed. Engl.*, 44:72-5, 2004.
Kitagawa, et al., "Functional porous coordination polymers," *Angew. Chem. Int. Ed.*, 43:2334-75, 2004.
Koder, et al., "Design and engineering of an $O_2$ transport protein," *Nature*, 458:305-9, 2009.
Koh, et al., "A porous coordination copolymer with over 5000 m2/g BET surface area," *J. Am. Chem. Soc.*, 131:4184-5, 2009.
Lan, et al., "A luminescent microporous metal-organic framework for the fast and reversible detection of high explosives," *Angew. Chem. Int. Ed.*, 48:2334-8, 2009.
Lee, et al., "A comparison of the H2 sorption capacities of isostructural metal-organic frameworks with and without accessible metal sites: [{Zn2(abtc)(dmf)2}3] and [{Cu2(abtc)(dmf)2}3] versus [(Cu2(abtc))3]," *Agnew. Chem. Int. Ed.*, 47:7741-5, 2008.
Li, et al., "Design and synthesis of an exceptionally stable and highly porous metal-organic framework," *Nature*, 402:276-9, 1999.
Lim, et al., "Cucurbit[6]uril: organic molecular porous material with permanent porosity, exceptional stability, and acetylene sorption properties," *Agnew. Chem.*, 120:3400-03, 2008.
Lin, et al., "High capacity hydrogen adsorption in Cu(II) tetracarboxylate framework materials: the role of pore size, ligand functionalization, and exposed metal sites," *J. Am. Chem. Soc.*, 131:2159-71, 2009.
Lin, et al., "Hydrogen, methane and carbon dioxide adsorption in metal-organic framework materials," *Top Curr. Chem.*, 293:35-76, 2010.
Lin, et al., "Modular synthesis of functional nanoscale coordination polymers," *Angew. Chem. Int. Ed.*, 48:650-8, 2009.
Liu, et al., "Increasing the density of adsorbed hydrogen with coordinatively unsaturated metal centers in metal-organic frameworks," *Langmuir*, 24:4772-7, 2008.
Liu, et al., "Metal-organic framework as a template for porous carbon synthesis," *J. Am. Chem. Soc.*, 130:5390-1, 2008.
Ma and Lin, "Unusual interlocking and interpenetration lead to highly porous and robust metal-organic frameworks," *Angew. Chem. Int. Ed.*, 48:3637-40, 2009.
Ma, et al., "Further investigation of the effect of framework catenation on hydrogen uptake in metal-organic frameworks," *J. Am. Chem. Soc.*, 130:15896-902, 2008.
Ma, et al., "Metal-organic framework from an anthracene derivative containing nanoscopic cages exhibiting high methane uptake," *J. Am. Chem. Soc.*, 130:1012-6, 2008.
Matsuda, et al., "Highly controlled acetylene accommodation in a metal-organic microporous material," *Nature*, 436:238-41, 2005.
McKinlay, et al., "Exceptional behavior over the whole adsorption-storage-delivery cycle for NO in porous metal organic frameworks," *J. Am. Chem. Soc.*, 130:10440-10444, 2008.
Millward and Yaghi, "Metal-organic frameworks with exceptionally high capacity for storage of carbon dioxide at room temperature," *J. Am. Chem. Soc.*, 127:17998-9, 2005.
Morris and Wheatley, "Gas storage in nanoporous materials," *Angew. Chem. Int. Ed.*, 47:4966-81, 2008.
Nelson, et al., "Supercritical processing as a route to high internal surface areas and permanent microporosity in metal-organic framework materials," *J. Am. Chem. Soc.*, 131:458-60, 2009.
Noro, et al., "A new, methane adsorbent, porous coordination polymer," *Angew. Chem. Int. Ed. Engl.*, 39:2081-4, 2000.
Park, et al., "Exceptional chemical and thermal stability of zeolitic imidazolate frameworks," *Proc. Natl. Acad. Sci. USA*, 103:10186-91, 2006.
Reid and Thomas, "Adsorption kinetics and size exclusion properties of probe molecules for the selective porosity in a carbon molecular sieve used for air separation," *J. Phys. Chem. B.*, 105:10619-29, 2001.

Reid and Thomas, "Adsorption of gases on a carbon molecular sieve used for air separation: linear adsorptives as probes for kinetic selectivity," *Langmuir*, 15:3206-18, 1999.
Rosi, et al., "Hydrogen storage in microporous metal-organic frameworks," *Science*, 300:1127-9, 2003.
Rosi, et al., "Rod packings and metal-organic frameworks constructed from rod-shaped secondary building units," *J. Am. Chem. Soc.*, 127:1504-18, 2005.
Roswell and Yaghi, "Effects of functionalization, catenation, and variation of the metal oxide and organic linking units on the low-pressure hydrogen adsorption properties of metal-organic frameworks," *J. Am. Chem. Soc.*, 128:1304-15, 2006.
Samsonenko, et al., "Microporous magnesium and manganese formates for acetylene storage and separation," *Chem. Asian J.*, 2:484-8, 2007.
Seo, et al., "A homochiral metal-organic porous material for enantioselective separation and catalysis," *Nature*, 404:982-6, 2000.
Serre, et al., "Role of solvent-host interactions that lead to very large swelling of hybrid frameworks," *Science*, 315:1828-31, 2007.
Shimomura, et al., "Porous coordination polymers towards gas technology," *Struct. Bond*, 132:51-86, 2009.
Spek, "Single-crystal structure validation with the program PLATON," *J. Appl. Cryst.*, 36:7-13, 2003.
Stang and Diederich, In: *Modern Acetylene Chemistry*, VCH, New York, 1995.
Tanaka, et al., "Anthracene array-type porous coordination polymer with host-guest charge transfer interactions in excited states," *Chem. Commun.*, pp. 3142-3144, 2007.
Tanaka, et al., "Storage and sorption properties of acetylene in jungle-gym-like open frameworks," *Chem. Asian J.*, 3:1343-9, 2008.
Thallapally, et al., "Acetylene absorption and binding in a nonporous crystal lattice," *Angew. Chem. Int. Ed. Engl.*, 45:6506-9, 2006.
Thallapally, et al., "Flexible (breathing) interpenetrated metal-organic frameworks for $CO_2$ separation applications," *J. Am. Chem. Soc.*, 130:16842-3, 2008.
Thomas, "Adsorption and desorption of hydrogen on metal—organic framework materials for storage applications: comparison with other nanoporous materials," *Dalton Trans.*, 1487-1505, 2009.
Thomas, "How far is the concept of isolated active sites valid in solid catalysts?" *Top Catal.*, 50:98-105, 2008.
Vitillo, et al., "Role of exposed metal sites in hydrogen storage in MOFs," *J. Am. Chem. Soc.*, 130:8386-96, 2008.
Wang, et al., "Enhancing $H_2$ uptake by "close-packing" alignment of open copper sites in metal-organic framework," *Angew. Chem. Int. Ed.*, 47:7263-6, 2008.
Welbes and Borovik, "Confinement of metal complexes within porous hosts: development of functional materials for gas binding and catalysis," *Acc. Chem. Res.*, 38:765-74, 2005.
Wu, et al., "High-capacity methane storage in metal-organic frameworks M2(dhtp): the important role of open metal sites," *J. Am. Chem. Soc.*, 131:4995-5000, 2009.
Xiang, et al., "Exceptionally high acetylene uptake in a microporous metal—organic framework with open metal sites," *J. Am. Chem. Soc.*, 131:12415-9, 2009.
Xiang, et al., "Open metal sites within isostructural metal-organic frameworks for differential recognition of acetylene and extraordinarily high acetylene storage capacity at room temperature," *Angew. Chem. Int. Ed. Engl.*, 49:4615-8, 2010.
Xu, et al., "Robust metal-organic framework enforced by triple-framework interpenetration exhibiting high H2 storage density," *Inorg. Chem.*, 47:6825-8, 2008.
Xue, et al., "New prototype isoreticular metal—organic framework $Zn_4O(FMA)_3$ for gas storage," *Inorg. Chem.*, 48:4649-51, 2009.
Xue, et al., "Structure, hydrogen storage, and luminescence properties of three 3D metal-organic frameworks with NbO and PtS topologies," *Crystal Growth & Design*, 8:2478-83, 2008.
Yildirim and Hartman, "Direct observation of hydrogen adsorption sites and nanocage formation in metal-organic frameworks," *Phys. Rev. Lett.*, 95:215504, 2005.
Zhang and Chen, "Exceptional framework flexibility and sorption behavior of a multifunctional porous cuprous triazolate framework," *J. Am. Chem. Soc.*, 130:6010-7, 2008.

Zhang and Chen, "Optimized acetylene/carbon dioxide sorption in a dynamic porous crystal," *J. Am. Chem. Soc.*, 131:5516-21, 2009.
Zhang and Kitagawa, "Supramolecular isomerism, framework flexibility, unsaturated metal center, and porous property of Ag(I)/Cu(I) 3,3',5,5'-tetrametyl-4,4'-bipyrazolate," *J. Am. Chem. Soc.*, 130:907-17, 2008.
Zhang, et al., "A highly connected porous coordination polymer with unusual chnnel structure and sorption properties," *Angew. Chem. Int. Ed.*, 48:5287-90, 2009.
Zhang, et al., "Versatile structure-direction roles of deep-eutectic solvents and their implication in the generation of porosity and open metal sites for gas storage," *Angew. Chem. Int. Ed.*, 48:3486-90, 2009.
Zhang, et al., "Zeolitic boron imidazolate frameworks," *Angew. Chem. Int. Ed. Engl.*, 48:2542-5, 2009.
Zhao, et al., "Hysteretic adsorption and desorption of hydrogen by nanoporous metal-organic frameworks," *Science*, 306:1012-5, 2004.
Zhou and Yildirim, "Nature and tunability of enhanced hydrogen binding in metal-organic frameworks with exposed transition metal sites," *J. Phys. Chem. C*, 112:8132, 2008.
Zhou, et al., "Enhanced H2 adsorption in isostructural metal-organic frameworks with open metal sites: strong dependence of the binding strength on metal ions," *J. Am. Chem. Soc.*, 130:15268-9, 2008.
Babarao, et al., "Storage and separation of CO2 and CH4 in silicalite, C168 schwarzite, and IRMOF-1: a comparative study from Monte Carlo simulation," *Langmuir*, 23:659-66, 2007.
Bai, et al., "The designed assembly of augmented diamond networks from predetermined pentanuclear tetrahedral units," *Angew. Chem. Int. Ed. Engl.*, 47:5344-7, 2008.
Busker, et al., "Isomer-selective vibrational spectroscopy of benzene-acetylene aggregates: comparison with the structure of the benzene-acetylene cocrystal," *Agnew. Chem. Intl. Ed. Engl.*, 47:10094-7, 2008.
Caskey, et al., "Dramatic tuning of carbon dioxide uptake via metal substitution in a coordination polymer with cylindrical pores," *J. Am. Chem. Soc.*, 130:10870-1, 2008.
Chen, et al., "A microporous metal-organic framework for gas-chromatographic separation of alkanes," *Angew. Chem. Int. Ed. .Engl.*, 45:1390-3, 2006.
Couck, et al., "An amine-functionalized MIL-53 metal-organic framework with large separation power for CO2 and CH4," *J. Am. Chem. Soc.*, 131:6326-7, 2009.
Czepirski and Jagiello, "Virial-Type Thermal Equation of Gas-Solid Adsorption," *Chem. Eng. Sci.*, 44:797-801, 1989.
Eddaoudi, et al. "Porous metal-organic polyhedra: 25 A cuboctahedron construsted from 12 Cu2(CO2)4 paddle-wheel building blocks," *J. Am. Chem. Soc.*, 123:4368-9, 2001.
Fang, et al., "A multifunctional metal-organic open framework with a bcu topology constructed from undecanuclear clusters," *Angew. Chem.*, 118:6272-6, 2006.
Fang, et al., "Microporous metal-organic framework constructed from heptanuclear zinc carboxylate secondary building units" *Chem. Eur. J.*, 12:3754-8, 2006.
Férey, et al., "Hydrogen adsorption in the nanoporous metal-benzenedicarboxylate M(OH)(02C-C6H4-CO2) (M=A13+,Cr3+), MIL-53," *Chem. Commun.*, pp. 2976-2977, 2003.
Furukawa, et al., "Independent verification of the saturation hydrogen uptake in MOF-177 and establishment of a benchmark for hydrogen adsorption in metal-organic frameworks," *J. Mater. Chem.*, 17:3197-204, 2007.
Jagiello, et al., "Adsorption near ambient temperatures of methane, carbon tetrafluoride, and sulfur hexafluoride on commercial activated carbons," *J. Chem. Eng. Data.*, 40:1288, 1955.
Lee, et al., "Synthesis and gas sorption properties of a metal-azolium framework material," *Inorg. Chem.*, 48:9971-3, 2009.
Ma, et al., "Framework-Catenation Isomerism in MOFs and Its Impact on Hydrogen Uptake," *J. Am. Chem. Soc.*, 129:1858-9, 2007.
Mu, et al., "A novel metal—organic coordination polymer for selective adsorption of $CO_2$ over $CH_4$," *Chem. Commun.*, pp. 2493-2495, 2009.

Mulfort and Hupp, "Chemical reduction of metal-organic framework materials as a method to enhance gas uptake and binding," *J. Am. Chem.*, 129:9604-5, 2007.

Myers and Prausnitz, "Thermodynamics of mixed-gas adsorption," *AIChE J.*, 11:121-7, 1965.

Rieter, et al., "Nanoscale coordination polymers for platinum-based anticancer drug delivery," *J. Am. Chem. Soc.*, 130:11584-5, 2008.

Wang, et al., "Bottom-up synthesis of porous coordination frameworks: apical substitution of a pentanuclear tetrahedral precursor," *Angew. Chem. Int. Ed.*, 48:5291-5, 2009.

Xiao, et al., "High-capacity hydrogen and nitric oxide adsorption and storage in a metal-organic framework," *J. Am. Chem. Soc.*, 129:1203-9, 2007.

Xie, et al., "Porous coordination polymer with flexibility imparted by coordinatively changeable lithium ions on the pore surface," *Inorg. Chem.*, 49:1158-65, 2010.

Yang and Zhong, "Molecular simulation of carbon dioxide/methane/hydrogen mixture adsorption in metal-organic frameworks," *J. Phys. Chem. B.*, 110:17776-83, 2006.

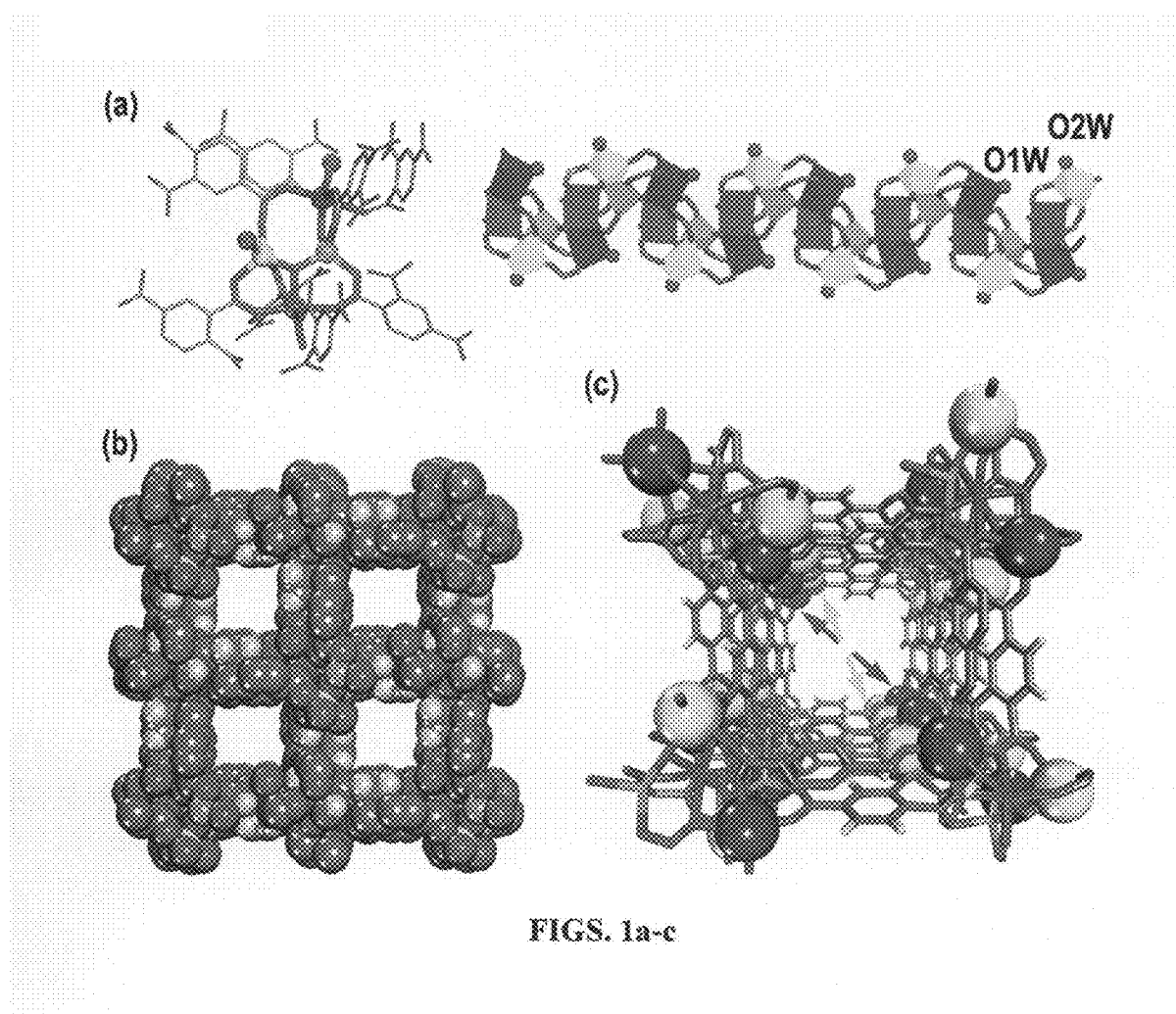
FIGS. 1a-c

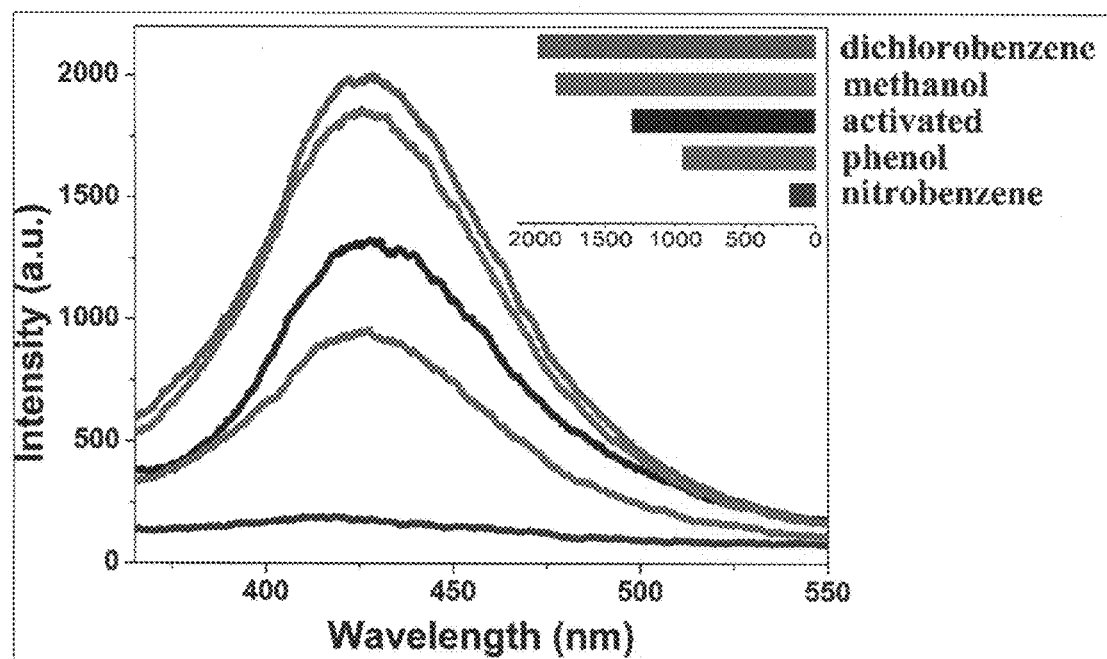
FIGS. 3a & b

ZN4(OH)2(1,2,4-BTC)2—A ROD PACKING MICROPOROUS METAL-ORGANIC FRAMEWORK WITH OPEN METAL SITES FOR SELECTIVE SEPARATION AND SENSING OF SMALL MOLECULES

The present application claims priority to U.S. Provisional Application Ser. No. 61/401,392 filed Aug. 12, 2010, the entire content of which is incorporated herein by reference.

This invention was made with government support under grant number CHE 0718281 from the National Science Foundation The government has certain rights in the invention.

BACKGROUND OF THE INVENTION

I. Field of the Invention

The present disclosure relates generally to the fields of chemistry and materials science. More particularly, it concerns metal-organic frameworks, compositions thereof and methods use thereof, including for gas storage, gas separation, catalysis and sensing.

II. Description of Related Art

Microporous metal-organic frameworks (MOFs) have been rapidly emerging as new type of porous materials for gas storage, separation, sensing and heterogeneous catalysis. The tunable pores and the immobilized functional sites within such microporous MOFs have enabled them to direct specific recognition of certain molecules, and thus for their highly selective guest sorption and separation. In fact, one of the most powerful $CO_2/CH_4$ separation materials has been realized in a rod-packing microporous MOF Mg-MOF-74 (Britt et al., 2009), exhibiting extremely high selectivity. Although thousands of MOFs have been synthesized and structurally characterized over the past two decades, the ones with open metal sites are still relatively few (Chen et al., 2010; Dinca and Long, 2008), this is mainly because such open metal sites are typically very reactive and tend to bind the atoms from the neighboring ligands to form the condensed structures. Also, few MOFs have been shown to be useful for selective sorption, separation and/or sensing of guest molecules. Accordingly, identifying and developing materials and compositions that exhibit one or more of these useful properties is desirable.

SUMMARY OF THE INVENTION

Disclosed herein is are new metal organic framework based on the formula comprising a repeat unit of the formula $Zn_4(OH)_2(1,2,4\text{-}BTC)_2$, wherein 1,2,4-BTC is benzene-1,2,4-tricarboxylate. In some embodiments, the method further comprises one or more than one type of guest molecule. In some embodiments, the guest molecule is a solvent molecule. In some embodiments, the solvent molecule is water, N,N'-diethylformamide or N,N'-dimethylformamide. In some embodiments, the guest molecule is a gas molecule. In some embodiments, the gas molecule is $H_2$, $N_2$, Ar, $O_2$, $CO_2$, NO, $NO_2$ or CO.

In some embodiments, the guest molecule is an alkane$_{(C1-6)}$, alkene$_{(C2-4)}$, alkyne$_{(C2-6)}$, alcohol$_{(C1-6)}$, arene$_{(C6-8)}$ or a substituted version of any of these. In some embodiments, the alkane$_{(C1-6)}$ is $CH_4$, $C_2H_6$, $C_3H_8$, $C_4H_{10}$, $C_5H_{12}$ or $C_6H_{14}$. In some embodiments, the alkane$_{(C1-6)}$ is a cycloalkane$_{(C3-6)}$ selected from the group consisting of $C_3H_6$, $C_4H_8$, $C_5H_{10}$ and $C_6H_{12}$. In some embodiments, the alkene$_{(C2-6)}$ is $C_2H_4$, $C_3H_6$, $C_4H_8$, $C_5H_{10}$ or $C_6H_{12}$. In some embodiments, the alkyne$_{(C2-6)}$ is $C_2H_2$. In some embodiments, the alcohol$_{(C1-6)}$ is methanol, ethanol, n-propanol, isopropanol, n-butanol or isobutanol. In some embodiments, the guest molecule is an arene$_{(C6-8)}$ or a substituted arene$_{(C6-8)}$. In some embodiments, the substituted arene$_{(C6-8)}$ is nitrobenzene, 1,2-dinitrobenzene, 1,3-dinitrobenzene, 1,4-dinitrobenzene, 1,2,4-trinitrobenzene or 1,3,5-trinitrobenzene.

In some embodiments, the MOF is substantially free from any solvent molecules. In some embodiments, the MOF has a weight percentage at least 90% attributable to repeat units of the formula $Zn_4(OH)_2(1,2,4\text{-}BTC)_2$. In some embodiments, the MOF has a weight percentage at least 95% attributable to repeat units of the formula $Zn_4(OH)_2(1,2,4\text{-}BTC)_2$. In some embodiments, the MOF has a weight percentage at least 99% attributable to repeat units of the formula $Zn_4(OH)_2(1,2,4\text{-}BTC)_2$.

In another aspect the present disclosure provides a method of storing a compound within a metal-organic framework (MOF) comprising:
(a) obtaining MOF comprising a repeat unit of the formula $Zn_4(OH)_2(1,2,4\text{-}BTC)_2$, wherein 1,2,4-BTC is benzene-1,2,4-tricarboxylate; and
(b) combining the MOF with a first compound such that the first compound is stored within the MOF.

In another aspect the present disclosure provides a method of detecting a compound using an MOF comprising:
(a) obtaining a MOF comprising a repeat unit of the formula $Zn_4(OH)_2(1,2,4\text{-}BTC)_2$, wherein 1,2,4-BTC is benzene-1,2,4-tricarboxylate;
(b) combining the MOF with a first compound such that the first compound enters the MOF to form an MOF guest complex; and
(c) comparing the luminescence intensity of the MOF with the luminescence intensity of the MOF guest complex so as to detect the first compound.

In another aspect the present disclosure provides a method of separating two or more compounds using an MOF comprising:
(a) obtaining a metal-organic framework (MOF) comprising a repeat unit of the formula $Zn_4(OH)_2(1,2,4\text{-}BTC)_2$, wherein 1,2,4-BTC is benzene-1,2,4-tricarboxylate;
(b) combining the MOF with a mixture comprising a first compound and a second compounds; and
(c) separating the two or more compounds based on their differential diffusion rate within the MOF.

In some embodiments, the first compound is in the form of a gas or a liquid. In some embodiments, the first compound is an alkane$_{(C1-6)}$, alkene$_{(C2-4)}$, alkyne$_{(C2-6)}$, alcohol$_{(C1-6)}$, arene$_{(C6-8)}$ or a substituted version of any of these. In some embodiments, the alkane$_{(C1-6)}$ is $CH_4$, $C_2H_6$, $C_3H_8$, $C_4H_{10}$, $C_5H_{12}$ or $C_6H_{14}$. In some embodiments, the alkane$_{(C1-6)}$ is $CH_4$. In some embodiments, the second compound is ethylene. In some embodiments, the alkane$_{(C1-6)}$ is a cycloalkane$_{(C3-6)}$ selected from the group consisting of $C_3H_6$, $C_4H_8$, $C_5H_{10}$ and $C_6H_{12}$. In some embodiments, the alkene$_{(C2-6)}$ is $C_2H_4$, $C_3H_6$, $C_4H_8$, $C_5H_{10}$ or $C_6H_{12}$. In some embodiments, the alkene$_{(C2-6)}$ is $C_2H_4$. In some embodiments, the second compound is $CO_2$. In some embodiments, the alkyne$_{(C2-6)}$ is $C_2H_2$. In some embodiments, the alcohol$_{(C1-6)}$ is methanol, ethanol, n-propanol, isopropanol, n-butanol or isobutanol. In some embodiments, the first compound is an arene$_{(C6-8)}$ or a substituted arene$_{(C6-8)}$. In some embodiments, the substituted arene$_{(C6-8)}$ is nitrobenzene, 1,2-dinitrobenzene, 1,3-dinitrobenzene, 1,4-dinitrobenzene, 1,2,4-trinitrobenzene or 1,3,5-trinitrobenzene. In some embodiments, the substituted arene$_{(C6-8)}$ is nitrobenzene. In some embodiments, the first compound is carbon dioxide. In some embodiments, the first compound is carbon monoxide. In some embodiments, the first compound is oxygen or nitrogen. In some embodiments, the first compound is $F_2$ or $Cl_2$. In some embodiments, the first compound is a noble gas. In some embodiments, the first compound is an alcohol. In some embodiments, the alcohol is methanol, ethanol, n-propanol or isopropanol.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

FIGS. 1a-c show the structure of MOF 1 showing (FIG. 1a) the coordination environments (left) and 1D rod chain (right), (FIG. 1b) the 1D channels of 6.2×5.7 Å$^2$ along a axis and (FIG. 1c) space-filling representation of the 1D channel exhibiting two immobilized open $Zn^{2+}$ sites (yellow and purple) on the pore surfaces of the framework (Zn1 green, Zn2 cyan, Zn3 yellow, Zn4 purple, O red, C gray, H white).

FIG. 2a shows gas sorption isotherms of MOF 1a for $C_2H_2$ (green square), $CO_2$ (red diamond) and $CH_4$ (blue triangle).

FIG. 3 shows emission spectra of solid 1a in different solvents when excited at 331 nm. The inset: The emission intensity at 428 nm.

FIG. 6 shows PXRD patterns of the as-synthesized 1 and the activated 1a.

DESCRIPTION OF ILLUSTRATIVE EMBODIMENTS

Figure 2A:
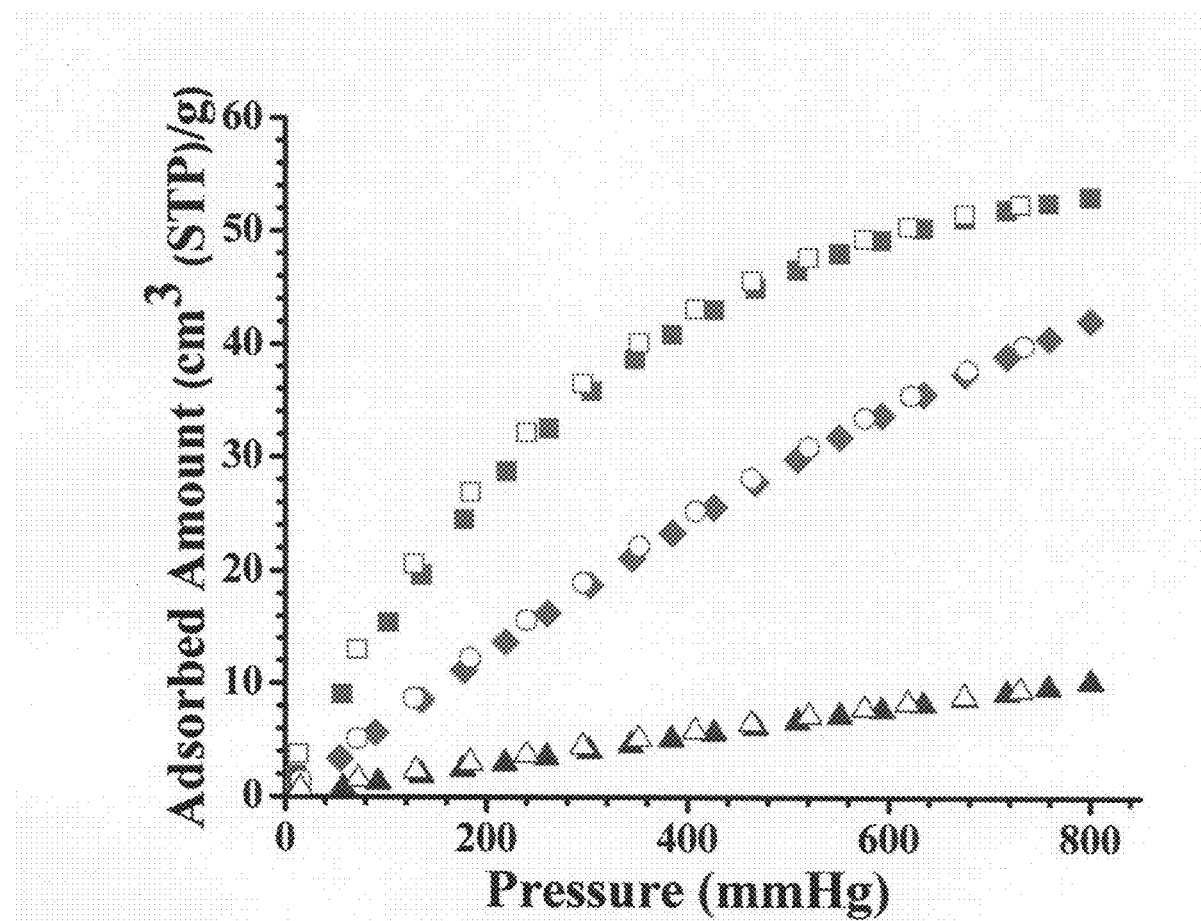
FIGS. 2a&b.

Disclosed herein are rod-packing robust microporous metal-organic frameworks with open $Zn^{2+}$ sites. These may be used for applications such as selective gas storage, selective gas sorption and/or separation, efficient sensing of certain compounds, for example, nitrobenzene, and catalysis.

I. Definitions

MOF 1 corresponds to the formula $[Zn_4(OH)_2(1,2,4\text{-}BTC)_2(H_2O)_2] \cdot \text{–}0.63\ DEF \cdot 3.5H_2O$ ( ) MOF 1a corresponds to the formula $[Zn_4(OH)_2(1,2,4\text{-}BTC)_2]$.

1,2,4-BTC refers to benzene-1,2,4-tricarboxylate.

DEF refers to N,N'-diethylformamide.

"Guest molecules" refer to molecules, including solvent molecules and gas molecules, that are enclosed within the pores or open sites of a framework material such as a MOF. Examples of guest molecules include, for example, methane, water, N,N'-dimethylformamide, N,N'-diethylformamide, ethanol and nitrobenzene.

"Metal-organic frameworks" (MOFs) are framework materials, typically three-dimensional, self-assembled by the coordination of metal ions with organic linkers exhibiting porosity, typically established by gas adsorption. The MOFs discussed and disclosed herein are at times simply identified by their repeat unit (see below), that is without brackets or the subscript n.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—CH$_2$CH$_2$—]$_n$—, the repeat unit is —CH$_2$CH$_2$—. The subscript "n" denotes the degree of polymerisation, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc. Note that for MOFs the repeat unit may also be shown without the subscript n.

"Pores" or "micropores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Interpenetrating metal-organic framework" is defined as metal-organic frameworks interlocked with one another.

"Multidentate organic linker" is defined as ligand having several binding sites for the coordination to one or more metal ions.

When used in the context of a chemical group, "hydrogen" means —H; "hydroxy" means —OH; "oxo" means =O; "halo" means independently —F, —Cl, —Br or —I; "amino" means —NH$_2$, and "nitro" means —NO$_2$.

For the groups and classes below, the following parenthetical subscripts further define the group/class as follows: "(Cn)" defines the exact number (n) of carbon atoms in the group/class. "(C≦n)" defines the maximum number (n) of carbon atoms that can be in the group/class, with the minimum number as small as possible for the group in question, e.g., it is understood that the minimum number of carbon atoms in the group "alkenyl$_{(C≦8)}$" or the class "alkene$_{(C≦8)}$" is two. For example, "alkoxy$_{(C≦10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkane" when used without the "substituted" modifier refers to a non-aromatic hydrocarbon consisting only of saturated carbon atoms and hydrogen and having a linear or branched, cyclo, cyclic or acyclic structure. Thus, as used herein cycloalkane is a subset of alkane. The compounds CH$_4$ (methane), CH$_3$CH$_3$ (ethane), CH$_3$CH$_2$CH$_3$ (propane), (CH$_2$)$_3$ (cyclopropane), CH$_3$CH$_2$CH$_2$CH$_3$ (n-butane), and CH$_3$CH(CH$_3$)CH$_3$ (isobutane), are non-limiting examples of alkanes. A "substituted alkane" differs from an alkane in that it also comprises at least one atom independently selected from the group consisting of N, O, F, Cl, Br, I, Si, P, and S. The following compounds are non-limiting examples of substituted alkanes: CH$_3$OH, CH$_3$Cl, nitromethane, CF$_4$, CH$_3$OCH$_3$ and CH$_3$CH$_2$NH$_2$.

The term "alkene" when used without the "substituted" modifier refers to a non-aromatic hydrocarbon having at least one carbon-carbon double bond and a linear or branched, cyclo, cyclic or acyclic structure. Thus, as used herein, cycloalkene is a subset of alkene. The compounds C$_2$H$_4$ (ethylene), CH$_3$CH=CH$_2$ (propene) and cylcohexene are non-limiting examples of alkenes. A "substituted alkene" differs from an alkene in that it also comprises at least one atom independently selected from the group consisting of N, O, F, Cl, Br, I, Si, P, and S.

The term "alkyne" when used without the "substituted" modifier refers to a non-aromatic hydrocarbon having at least one carbon-carbon triple bond and a linear or branched, cyclo, cyclic or acyclic structure. Thus, as used herein, cycloalkene is a subset of alkene. The compounds C$_2$H$_2$ (acetylene), CH$_3$C≡CH (propene) and cylcooctyne are non-limiting examples of alkenes. A "substituted alkene" differs from an alkene in that it also comprises at least one atom independently selected from the group consisting of N, O, F, Cl, Br, I, Si, P, and S.

The term "alcohol" when used without the "substituted" modifier corresponds to an alkane, as defined above, wherein at least one of the hydrogen atoms has been replaced with a hydroxy group. Alcohols have a linear or branched, cyclo, cyclic or acyclic structure. The compounds methanol, ethanol and cyclohexanol are non-limiting examples of alcohols. A "substituted alkane" differs from an alcohol in that it also comprises at least one atom independently selected from the group consisting of N, F, Cl, Br, I, Si, P, and S.

The term "arene" when used without the "substituted" modifier refers to an hydrocarbon having at least one six-membered aromatic ring. One or more alkyl, alkenyl or alkynyl groups may be optionally attached to this ring. Also this ring may optionally be fused with other rings, including non-aromatic rings. Benzene, toluene, naphthalene, and biphenyl are non-limiting examples of arenes. A "substituted arene" differs from an arene in that it also comprises at least one atom independently selected from the group consisting of N, O, F, Cl, Br, I, Si, P, and S. Phenol and nitrobenzene are non-limiting examples of substituted arenes.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on a carbon atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

The term "saturated" when referring to an atom means that the atom is connected to other atoms only by means of single bonds.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Synthetic Methods

The metal-organic framework [Zn$_4$(OH)$_2$(1,2,4-BTC)$_2$(H$_2$O)$_2$]·xG (1,2,4-BTC is benzene-1,2,4-tricarboxylate; G=one or more optional guest molecules) may be made using the methods outlined in the examples section below.

For example, MOF 1 can be readily constructed by the solvothermal reaction of $Zn(NO_3)_2 \cdot 6H_2O$ and 1,2,4-$H_3$BTC in DEF/ethanol/$H_2O$ mixture at 65° C. for 48 hrs as colorless crystals. It was formulated as $[Zn_4(OH)_2(1,2,4\text{-BTC})_2(H_2O)_2] \cdot -0.63\text{DEF} \cdot 3.5H_2O$ (DEF=N,N'-diethylformamide) by elemental analysis and single-crystal X-ray diffraction studies, and the phase purity of the bulk material was independently confirmed by powder X-ray diffraction (PXRD) (details in Examples section below).

Figure 5:
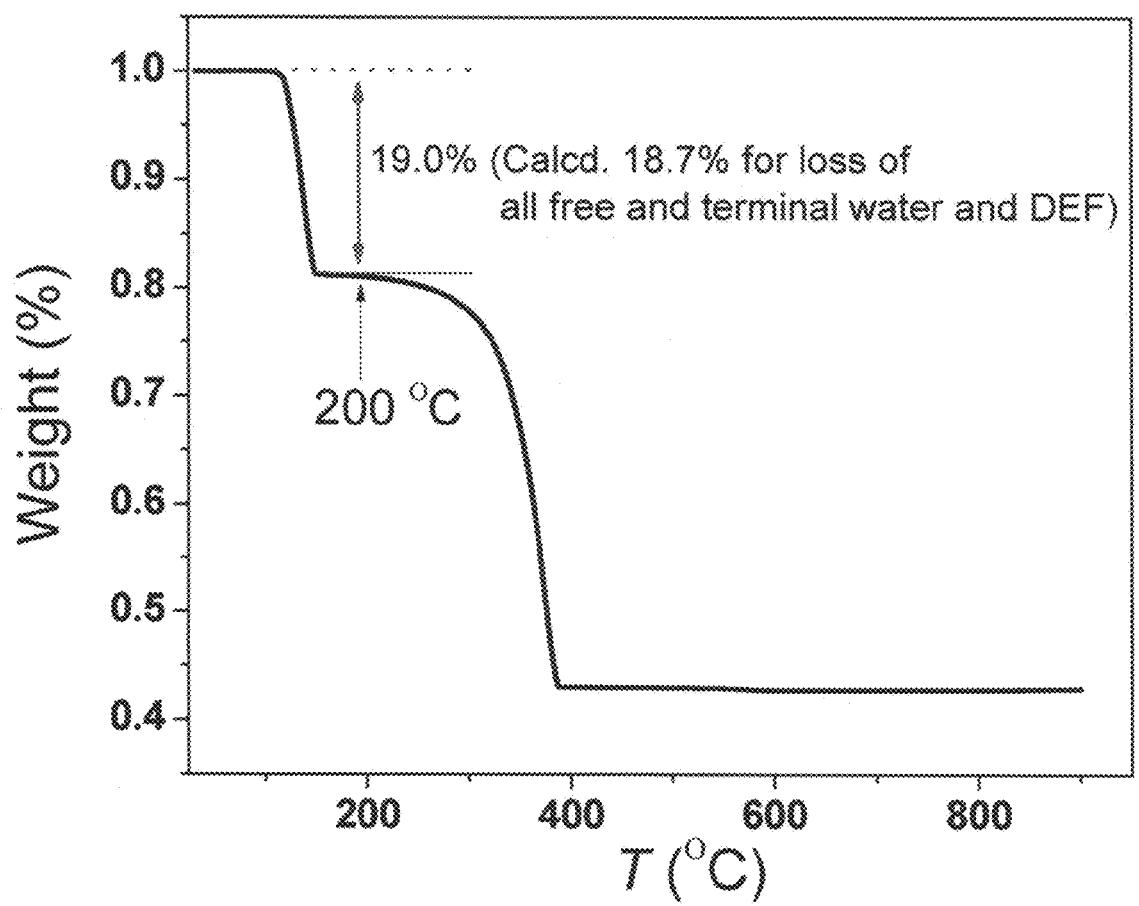
FIG. 5 shows TGA traces of 1 ranging from room temperature to 900° C.
Figure 6:
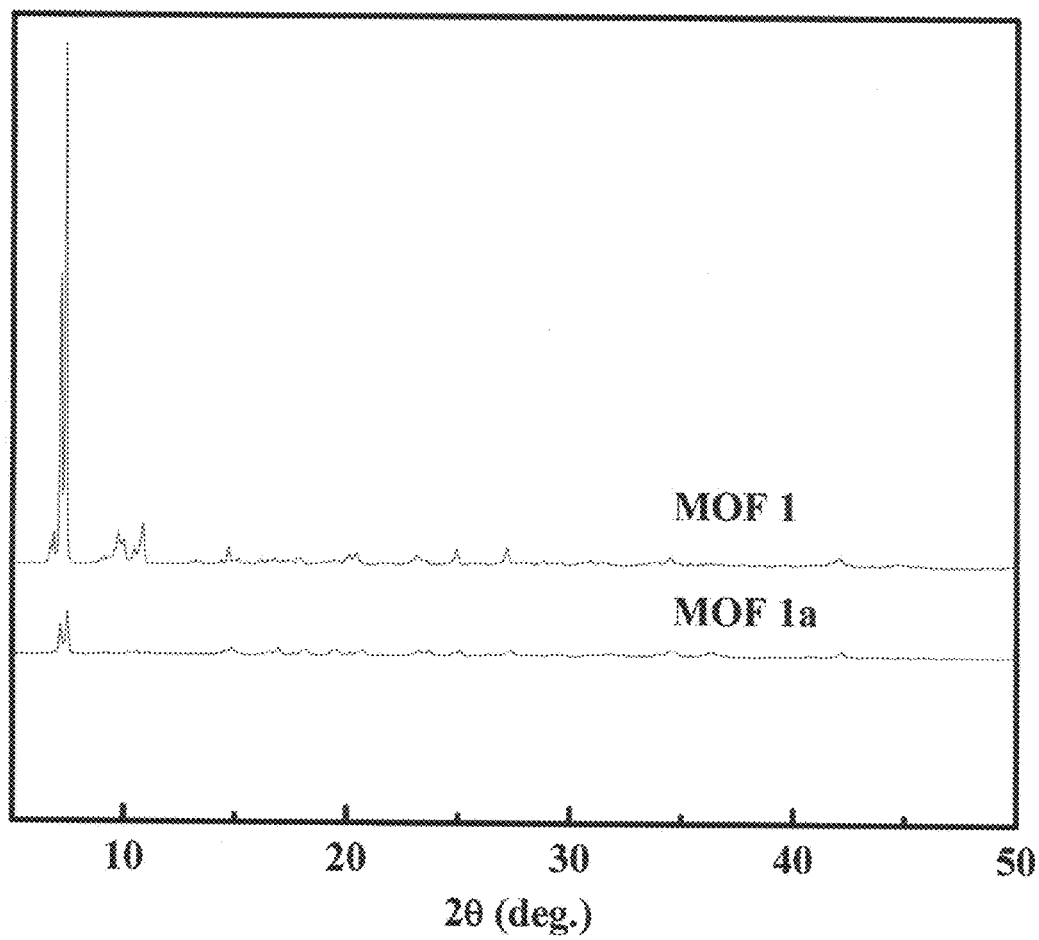

The X-ray single crystal structure of MOF 1 exhibits a three-dimensional rod-packing framework structure with one-dimensional pores along a axis of about 6.2×5.7 Å$^2$, which are filled with terminal water and guest solvent molecules. The void space accounts approximately 41.1% of the whole crystal volume (1322.9 Å$^3$ out of the 3217.7 Å$^3$ per unit cell volume) by PLATON analysis (Spek, 2003). TGA studies indicate that the terminal water and guest molecules can be readily released in the temperature range of 25 to 150° C. to form the guest free phase MOF 1a, which is stable up to 200° C. (FIG. 5). The PXRD pattern of MOF 1a is basically identical to that of as-synthesized 1 (FIG. 6), indicating that the framework is robust, thus the open metal sites (Zn3 and Zn4) can be generated by the removal of guest molecules after the thermal activation (FIG. 1c).

The methods described above can be further modified, optimized and scaled up using the principles and techniques of chemistry and/or materials science as applied by a person skilled in the art. Such principles and techniques are taught, for example, in Chen et al. (2005), which is incorporated by reference herein.

III. Properties and Uses of MOFs

Figure 7:
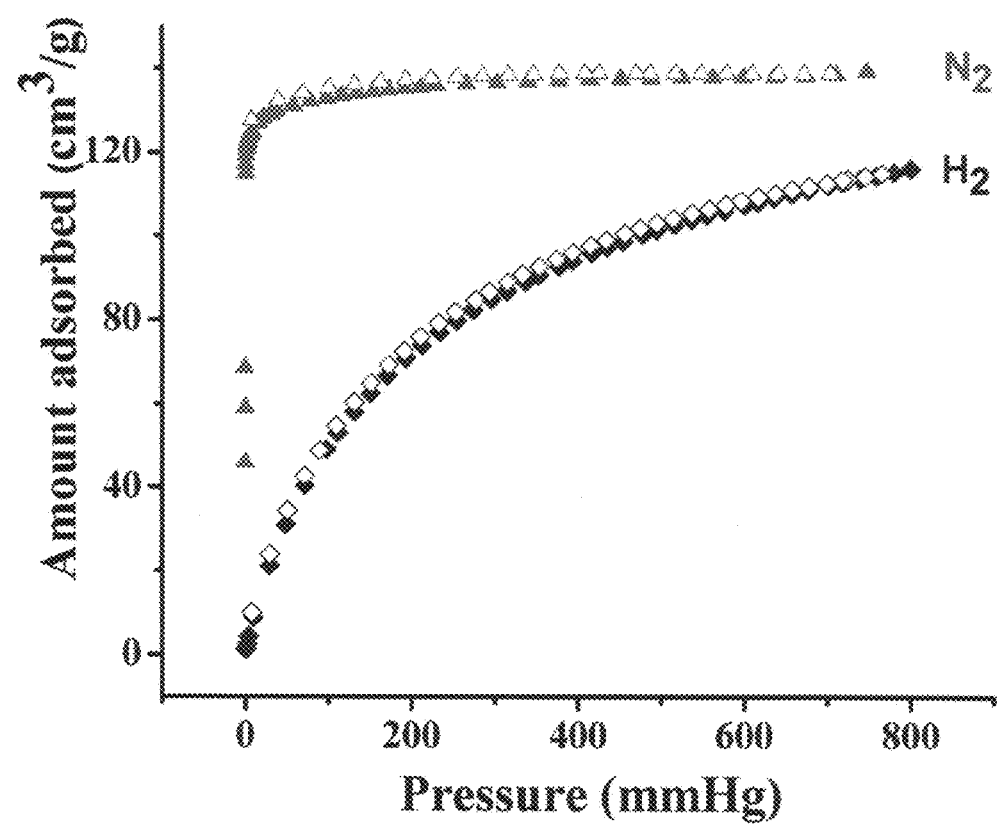
FIG. 7 shows gas sorption isotherms of MOF 1a for $N_2$ and $H_2$ at 77 K.
Figure 8:
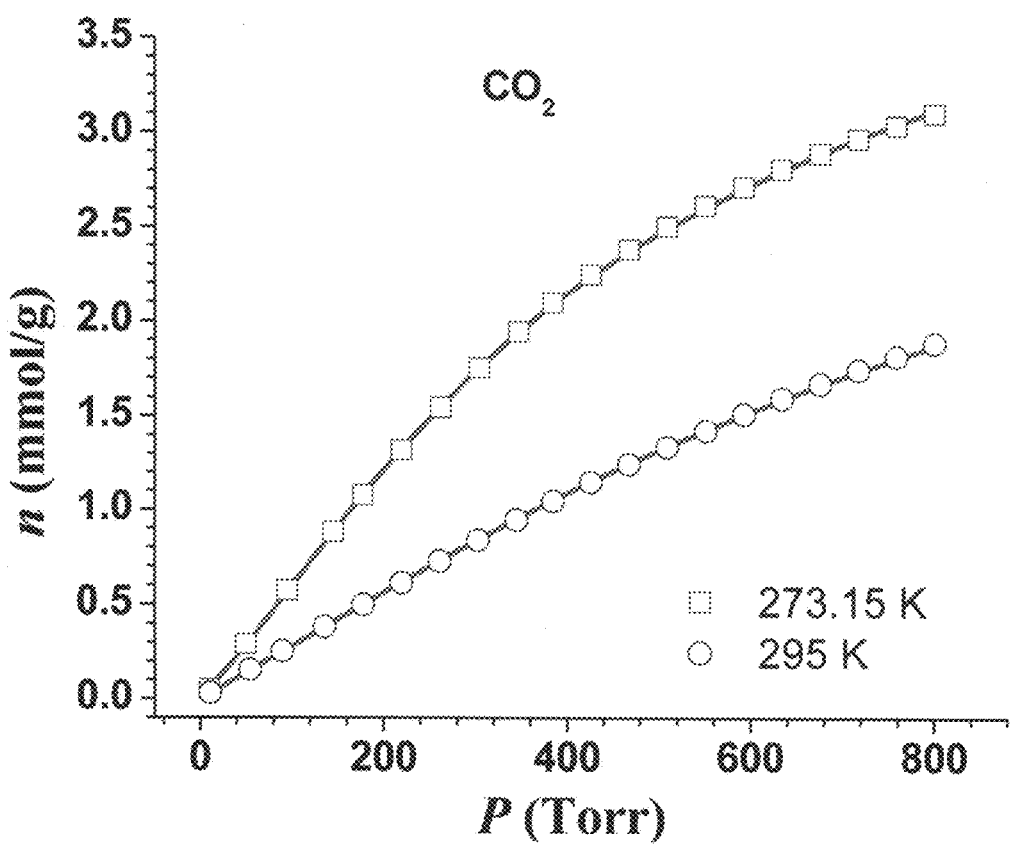
FIG. 8 shows adsorption isotherms for the uptake of $CO_2$ within the 1a at 273.2 K (square) and 295.0 K (cycle). The red solid lines represent the fitting by using the virial expression.
Figure 9:
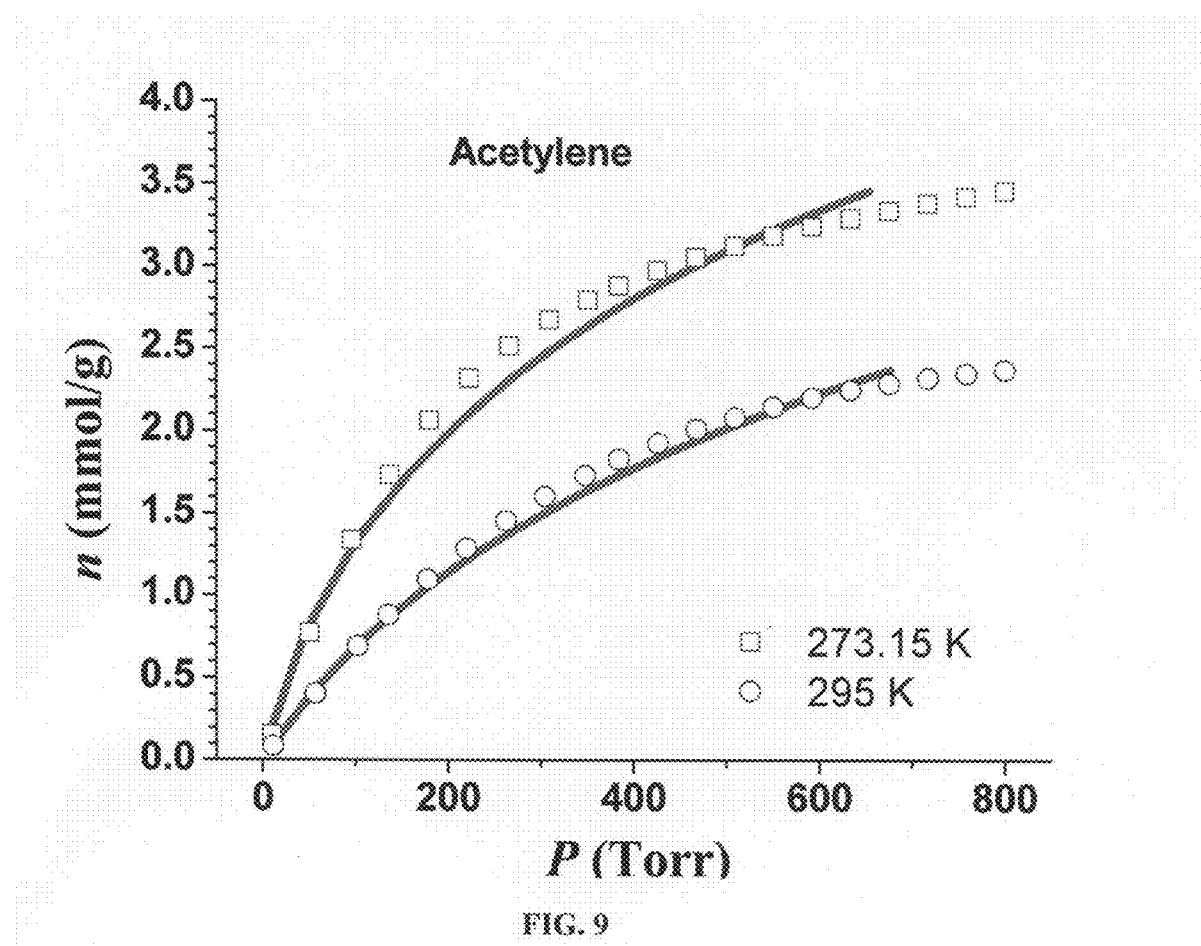
FIG. 9 shows adsorption isotherms for the uptake of acetylene within the 1a at 273.2 K (square) and 295.0 K (cycle). The red solid lines represent the fitting by using the virial expression.
Figure 10:
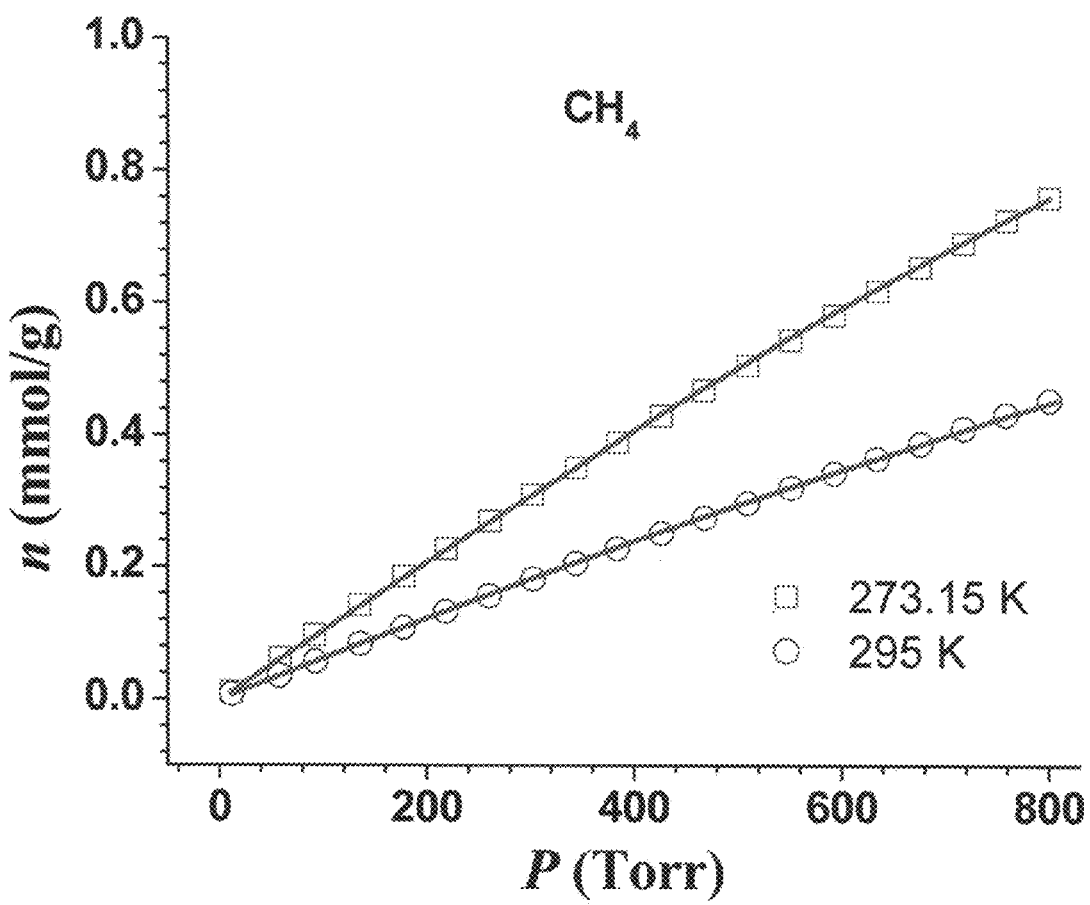
FIG. 10 shows adsorption isotherms for the uptake of methane within the 1a at 273.2 K (square) and 295.0 K (cycle). The red solid lines represent the fitting by using the virial expression.
Figure 11:
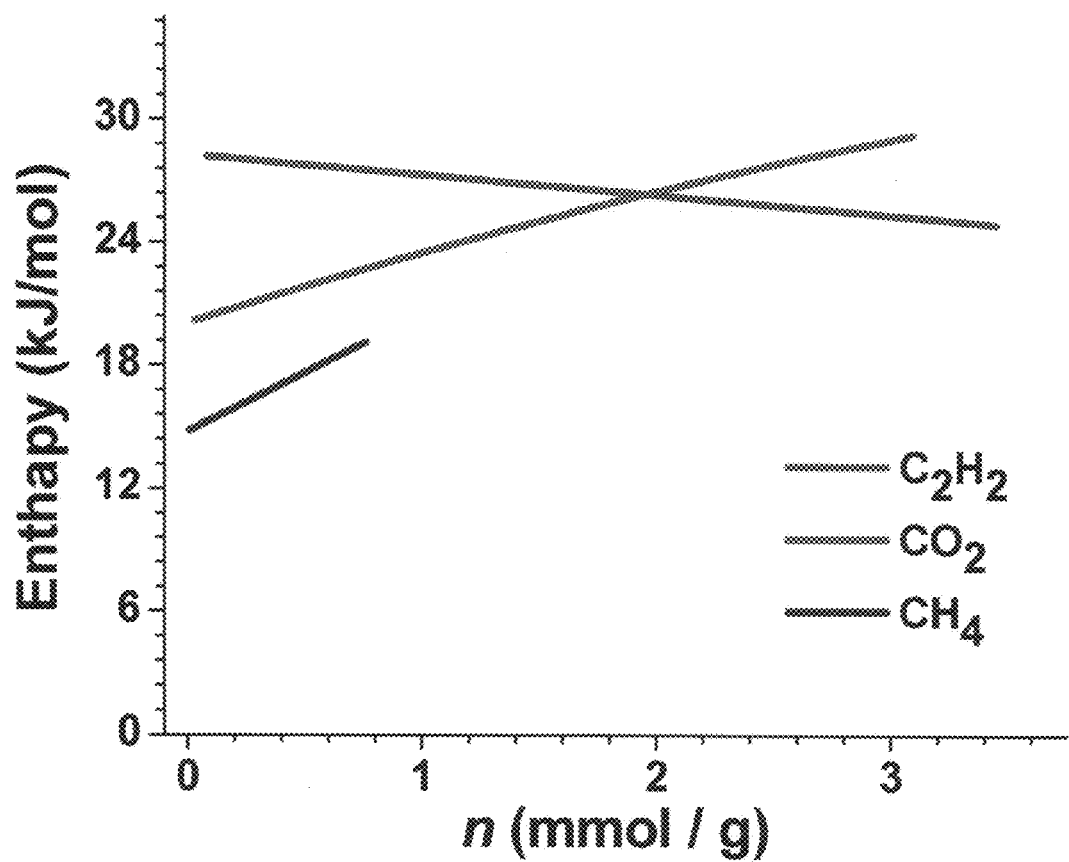
FIG. 11 shows coverage dependencies of the isosteric heats of adsorption for $C_2H_2$ (green), $CO_2$ (red) and $CH_4$ (blue) in the 1a calculated from fits of their 273.2 and 295.0 K isotherms using the virial method.
Figure 12:
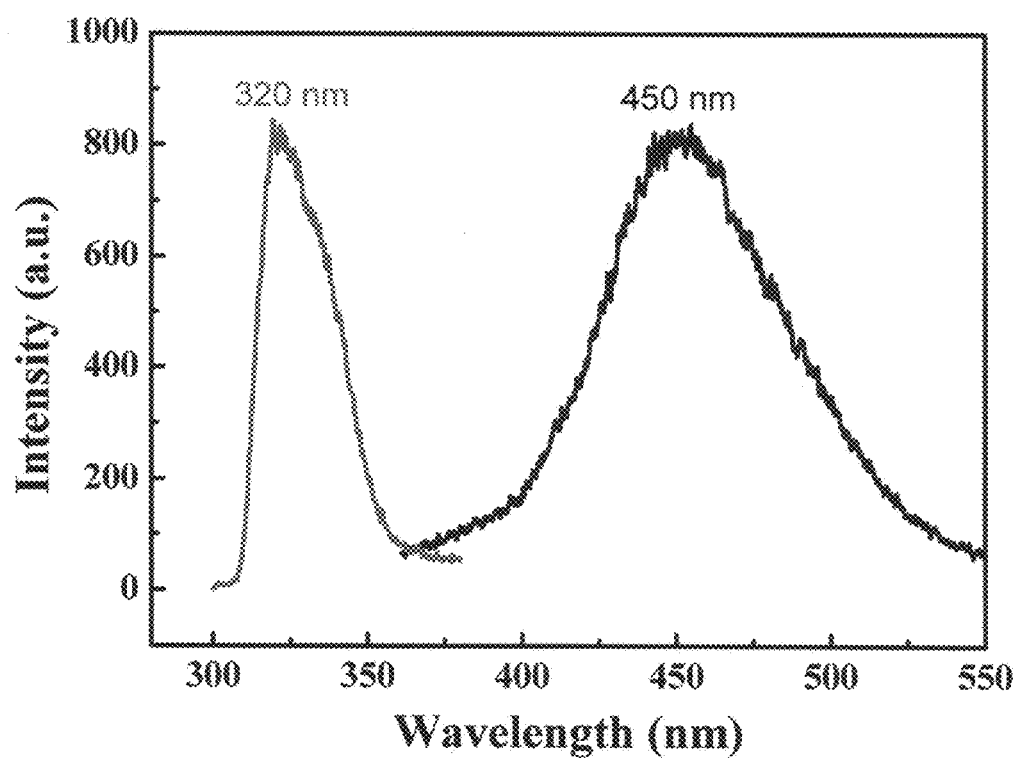
FIG. 12 shows excitation (red) and emission (black) spectra of BTC ligand.
Figure 13:
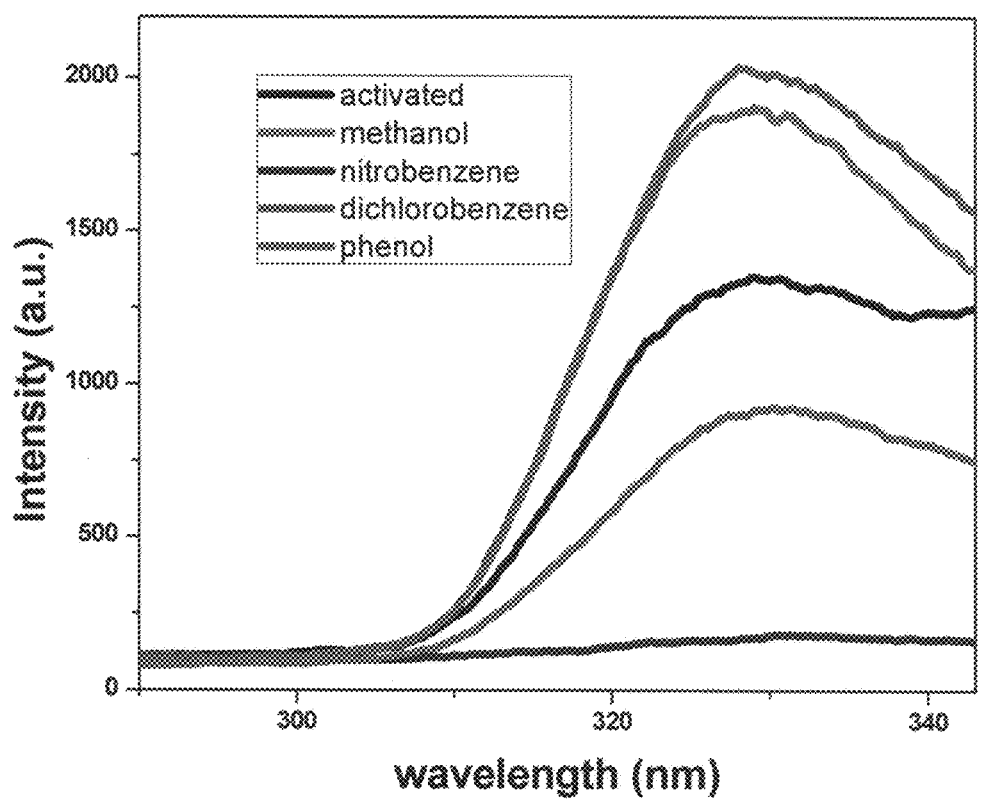
FIG. 13 shows excitation spectra of 1a in different solvent.

In some embodiments the MOFs disclosed herein my be used for gas separation, gas storage and/or gas sensing. Many of these applications result from the unique micropores of the MOFs. The permanent micropore feature of the activated MOF 1a was further established by $N_2$ sorption isotherm at 77 K, which displays typical type-I sorption behavior (FIG. 7), with the BET surface area and pore volume of 408 m$^2$ g$^{-1}$ and 0.205 cm$^3$ g$^{-1}$, respectively. Its potential application was thus examined on the gas and vapor selective separation. As shown in FIG. 2a, MOF 1a takes up differential amount of $C_2H_2$ (53 cm$^3$/g), $CO_2$ (42 cm$^3$/g) and $CH_4$ (10 cm$^3$/g) at 295 K and 1 atm, highlighting its potential application for the separation of $C_2H_2/CH_4$ and $CO_2/CH_4$. The adsorption enthalpies of 1a to $C_2H_2$, $CO_2$ and $CH_4$ gases at low coverage are of 28.2, 20.2 and 14.8 kJ/mol, respectively, as calculated based on virial method, a well established and reliable methodology from fits of their adsorption isotherms at 273 and 295 K (Roswell and Yaghi, 2006, which are both incorporated herein by reference). From these results, the Henry's constant ($K_H$) and the Henry's Law selectivity $S_{ij} = K_{Hi}/K_{Hj}$ for gas component i over j at 295 K are also given in Table 1. The separation selectivity for $C_2H_2/CH_4$ and $CO_2/CH_4$ mixtures is 14.7 and 4.5, respectively. The open $Zn^{2+}$ sites contribute significantly to the stronger interactions between the pore surface with acetylene molecules. The acetylene adsorption enthalpy at the coverage of 0.16 mmol/g of 28.1 kJ/mol of MOF 1a is even higher than that of 24.0 kJ/mol of Zn-MOF-74 with well orientated open $Zn^{2+}$ sites (Xiang et al., 2010), leading to its high separation selectivity of 14.7 for the $C_2H_2/CH_4$ separation.

TABLE 1

Virial Coefficients Employed to Fit the 273.2 K and 295.0 K Adsorption Isotherm data of $C_2H_2$, $CO_2$ and $CH_4$ for MOF 1a.

|  | $C_2H_2$ | $CO_2$ | $CH_4$ |
|---|---|---|---|
| a0 | −3397.9 ± 163.1 | −1383.4 ± 247.2 | −1774.2 ± 43.8 |
| a1 | 118.0 ± 6.7 | −1304.9 ± 125.1 | −689.3 ± 150.0 |
| a2 | 0 ± 0 | 60.1 ± 3.5 | 0 ± 0 |
| a3 | 0 ± 0 | 0 ± 0 | 0 ± 0 |
| a4 | 0 ± 0 | 0 ± 0 | 0 ± 0 |
| a5 | 0 ± 0 | 0 ± 0 | 0 ± 0 |
| a6 | 0 ± 0 | 0 ± 0 | 0 ± 0 |
| b0 | 16.2 ± 0.6 | 9.6 ± 0.8 | 13.4 ± 0.2 |
| b1 | 0 ± 0 | 4.3 ± 0.4 | 2.5 ± 0.5 |
| b2 | 0 ± 0 | 0 ± 0 | 0.2 ± 0.1 |
| b3 | 0 ± 0 | 0 ± 0 | 0 ± 0 |
| R* | 0.964 | 1.000 | 0.998 |
| $K_H$ | 0.009337 | 0.002856 | 0.000636 |
| $S_{i/CH4}$ | 14.7 | 4.5 | |

*R is the correlation coefficient.

Figure 2B:
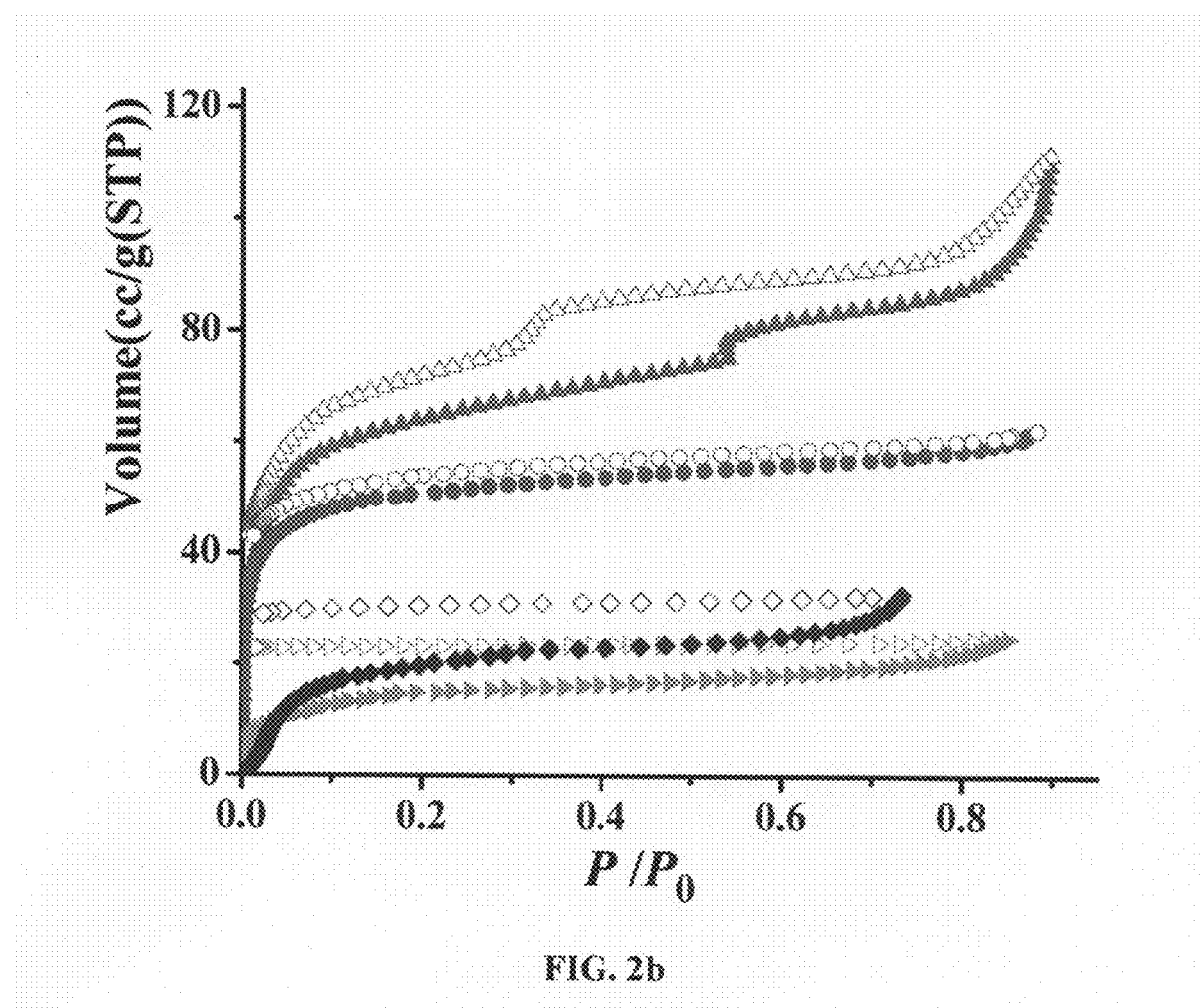
FIG. 2b shows vapor sorption isotherms of MOF 1a for methanol (red triangle), ethanol (green circle), n-propanol (blue diamond) and isopropanol (orange triangle) at 295 K (adsorption, solid color; desorption, empty color).
Figure 4:
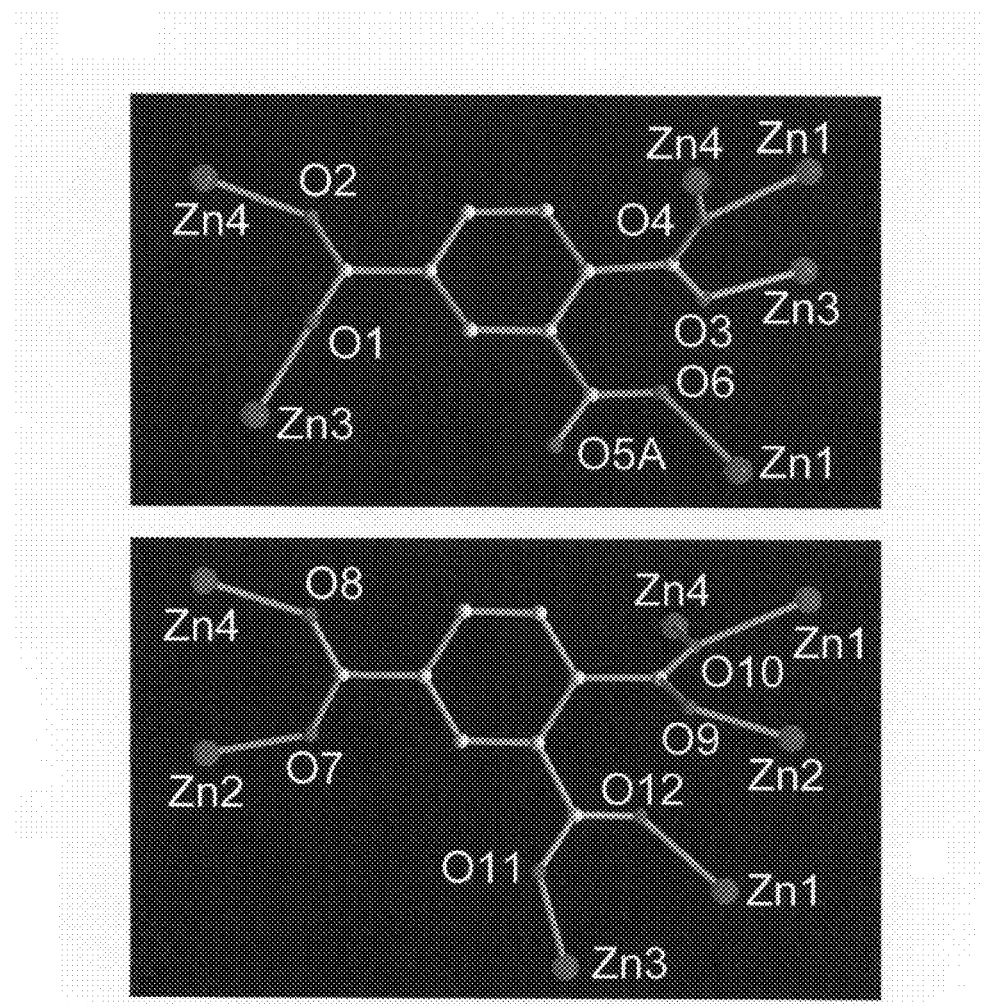
FIG. 4 shows the coordination mode of two BTC ligands.

The MOB of the present invention provide unique sorption isotherms and the highly selective sorption behaviors. For example MOF 1a provides such with respect to different alcohols at 295 K. The existence of the open metal sites leads to hysteresis sorption. The small methanol molecules are able to bind the two open metal sites step by step as clearly shown in the methanol sorption isotherm at $P/P_0$=0.54 and 0.84, respectively. Without being bound by theory, it may be that the orientation of the two $Zn^{2+}$ open metal sites has limited their binding of larger alcohols simultaneously, so the sorption isotherms of 1a for ethanol, n-propanol and isopropanol do not exhibit two-step adsorption, and the saturated sorption capacity for ethanol (62.2 cm$^3$·g$^{-1}$), n-propanol (32.6 cm$^3$·g$^{-1}$) and isopropanol (24.7 cm$^3$·g$^{-1}$) are much smaller than the saturated methanol adsorption amount of 111.7 cm$^3$·g$^{-1}$ (FIG. 2b). This features MOF 1a as a very promising separation material for these small alcohols.

Figure 14:
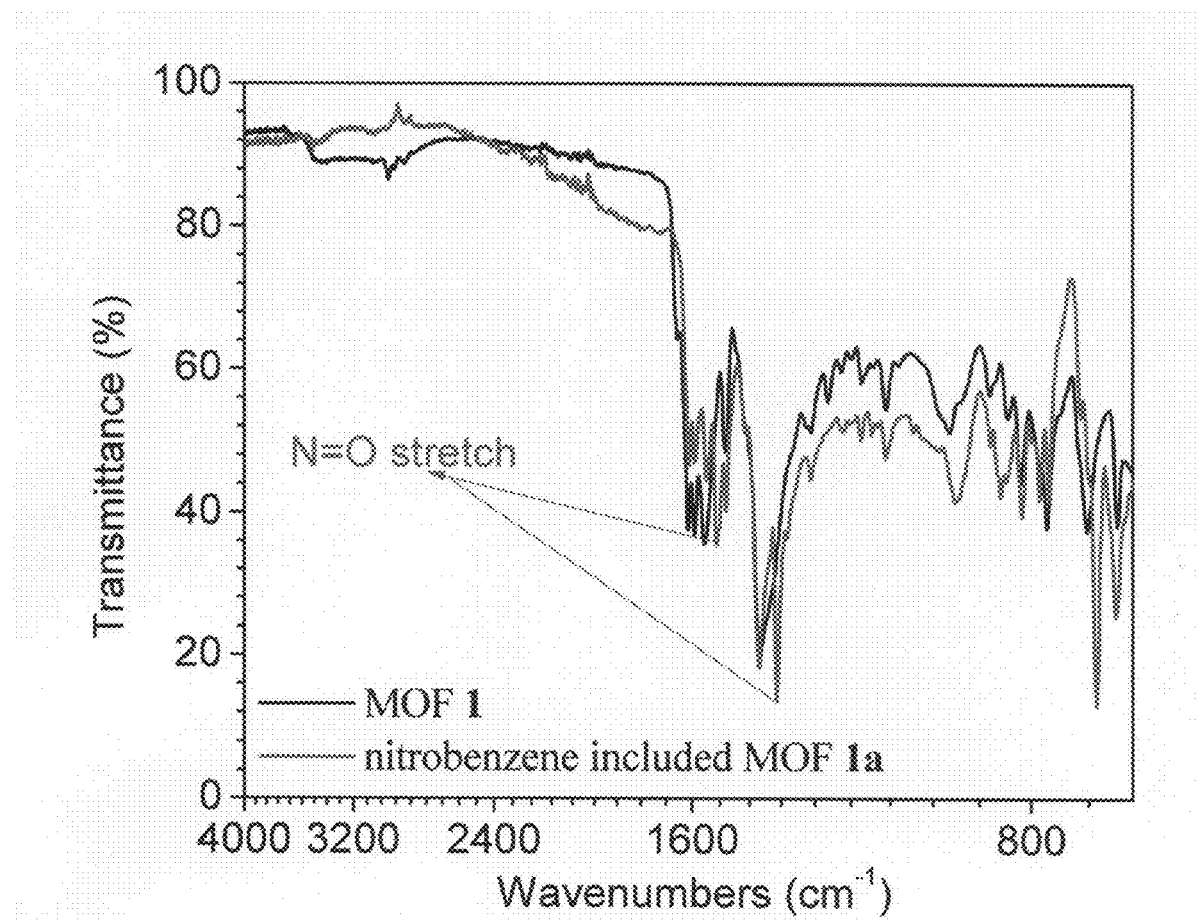
FIG. 14 shows IR spectra (4000-650 cm$^{-1}$) of MOF 1 (black) (2979 (w), 1612 (m), 1592 (m), 1559 (m), 1493 (m), 1393 (s), 1254 (w), 1211 (w), 1132 (m), 1077 (w), 945 (m), 871 (m), 839 (m), 817 (m), 774 (m), 713 (m), 670 (m)) and nitrobenzene included MOF 1a (red) (1611 (w), 1592 (w), 1554 (w), 1522 (m), 1494 (m), 1396 (s), 1347 (s), 1255(w), 1173(w), 1133 (w), 1078 (m), 934 (m), 871 (s), 852 (m), 816 (m), 786 (m), 772 (m), 723 (m), 700 (s), 673 (s)).

The MOFs of the present disclosure may also be used for sensing compound, for example sensing aromatic compounds. The potential of MOF 1a for the sensing of aromatic compounds was therefore explored. As shown in FIGS. 3a & b, the addition of small amount of different aromatic compounds and methanol affect the luminescence intensities differently. Of particular importance is the significant quenching effect of nitrobenzene on the luminescence intensities of MOF 1a. The inclusion of nitrobenzene within MOF 1a was confirmed by IR spectra in which the nitrobenzene included. MOF 1a exhibits new peaks at 1522 and 1347 cm$^{-1}$ attributed from N=O stretch of nitrobenzene (FIG. 14) (Sorrell, 2006). Such quenching effect is attributed to the charge transfer electron transitions from the benzene ring of BTC ligands to nitrobenzene due to the electron-deficient property of nitrobenzene and the π-π interactions between MOF 1a framework and nitrobenzene molecules.

IV. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Materials and Measurements.

All reagents and solvents were used as received from commercial suppliers without further purification. TGA (thermal gravimetric analysis) was performed under a nitrogen atmosphere with a heating rate of 3° C./min using a Shimadzu TGA-50 thermogravimetric analyzer. Powder X-ray diffraction (XRD) data were collected on a RIGAMU D/MAX 2550/PC X diffractometer with CuKα radiation. Analyses for C, H and N were carried out on a Flash EA1112 analyzer. $N_2$, $H_2$, $C_2H_2$, $CH_4$ and $CO_2$ adsorption isotherms were measured on ASAP 2020. A Coulter Omnisorp 100cx analyzer was used to measure methanol, ethanol, propanol, isopropanol sorption isotherm for activated 1a formed by heating of the as-synthesized MOF 1a at the temperature of 150° C. under high vacuum overnight. Fourier-transform (FT-IR) spectra (4000-650 $cm^{-1}$) were measured with a Bruker Equinox 55 FTIR spectrometer on KBr disks.

Fluorescence Measurements.

The fluorescence properties of MOF 1 and solvent included MOF 1a were investigated in the solid state at room temperature. A fresh sample (30 mg) of MOF 1 was activated and then immersed into methanol solvent (20 mL) with different organic solvent (0.2 mL) to form solvent included MOF 1a which was collected by filtration and drying for 24 hrs at 20° C. The sample was pressed on a glass slide for the photoluminescence studies. The photoluminescence (PL) spectra were recorded by a Hitachi F4500 fluorescence spectrometer. The photomultiplier tube voltage was 700 V and the scan speed was 240 nm/min, and the slit widths were 1.0 and 2.5 nm, respectively, for excitation and emission spectra.

Derivation of the Isosteric Heats of Adsorption:

A virial type expression of the following form was used to fit the combined isotherm data for a given material at 295.0 and 273.2 K (Roswell and Yaghi, 2006).

$$\ln P = \ln N + 1/T \sum_{i=0}^{m} a_i N^i + \sum_{i=0}^{n} b_i N^i. \quad (1)$$

Here, P is the pressure expressed in Torr, N is the amount adsorbed in mmol/g, T is the temperature in K, $a_i$ and $b_i$ are virial coefficients, and m, n represents the number of coefficients required to adequately describe the isotherms. The equation was fit using the statistical software package SPSS 16.0. m and n were gradually increased until the contribution of extra added a and b coefficients was deemed to be statistically insignificant towards the overall fit, as determined using the average value of the squared deviations from the experimental values was minimized. In all cases, $m \leq 6$ and $n \leq 3$. The values of the virial coefficients $a_0$ through $a_m$, were then used to calculate the isosteric heat of adsorption using the following expression.

$$Q_{st} = -R \sum_{i=0}^{m} a_i N^i. \quad (2)$$

Here, $Q_{st}$ is the coverage-dependent isosteric heat of adsorption and R is the universal gas constant of 8.3147 J $K^{-1}$ $mol^{-1}$. From these results, the Henry's constant ($K_H$) is calculated from where T is temperature.

$$K_H = \exp(-b_0) \cdot \exp(-a_0/T)$$

See Czepirski and Jagiello (1989); Jagiello et al. (1995); Furukawa et al. (2007); and Rahul Banerjee et al. (2009), all of which are incorporated herein by reference.

The Henry's Law selectivity for gas component i over j at 295 K is calculated based on equation:

$$S_{ij} = K_{Hi}/K_{Hj}$$

Synthesis of MOF 1:

1,2,4-BTC (0.2 mmol, 42 mg), $Zn(NO_3)_2 \cdot 6H_2O$ (0.3 mmol, 89 mg), DEF (3 mL), $H_2O$ (2 mL) and ethanol (2 mL) were placed in a 23 mL glass vial, which was sealed and heated to 65° C. for 48 h, and then cooled to room temperature. The colorless crystals formed were collected and air-dried (65% based on $Zn(NO_3)_2 \cdot 6H_2O$). Elemental analysis (%) calcd for $[Zn_4(OH)_2(1,2,4\text{-btc})_2(H_2O)_2] \cdot 0.63DEF \cdot 3.5H_2O$: C, 29.11; H, 3.00; N, 1.01. Found: C, 28.73; H, 3.05; N, 1.22.

Crystal Structure Determination:

Intensity data for MOF 1 were collected at 90.0(5) K on a Nonius KappaCCD diffractometer using graphite-monochromated MoK radiation. The structure was solved by direct methods and subsequent difference Fourier syntheses, and refined using the SHELXTL software package. The H atoms on the ligands and coordinated $H_2O$ were placed in idealized positions and refined using a riding model. The unit cell includes a large region of disordered solvent molecules, which could not be modeled as discrete atomic sites. PLATON/SQUEEZE were employed to calculate the diffraction contribution of the solvent molecules and, thereby, to produce a set of solvent-free diffraction intensities. Crystal data for 1: $C_{18}H_{12}O_{16}Zn_4$, M=745.76, orthorhombic, space group $P2_12_12_1$, a=10.9180(6) Å, b=17.1253(14) Å, c=17.2092(15) Å, V=3217.7(4) $Å^3$, Z=4. Dc=1.539 $g \cdot cm^{-3}$, μ=3.005 $mm^{-1}$, T=293 K, F(000)=1472, 5837 reflections collected, 5647 independent reflections ($R_{int}$=0) which were used in all the calculations. After the refinement cycles, reliability factors were R1=0.0208, wR2=0.0540 for [I>2.0σ(I)], and R1=0.0220, wR2=0.0547 for all 5647 data. CCDC-774968.

All of the methods disclosed and claimed herein can be made and executed without undue experimentation in light of the present disclosure. While the compositions and methods of this invention have been described in terms of particular embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

Britt et al., *Proc. Natl. Acad. Sci. USA*, 106:20637, 2009.
Chen et al., *Acc. Chem. Res.*, DOI:10.1021-2010-00023, 2010.
Chen et al., *Angew. Chem. Int. Ed.*, 44:4745-4749, 2005.
Czepirski and Jagiello, *J. Chem. Eng. Sci.*, 44:797, 1989.
Dinca and Long, *Angew. Chem. Int. Ed.*, 47:6766, 2008.
Furukawa et al., *J. Mater. Chem.*, 17:3197, 2007.
Huang et al., *Chem. Mater.*, 21:541, 2009.
Jagiello et al., *J. Chem. Eng. Data*, 40:1288, 1995.
Lan et al., *Chem. Int. Ed.*, 48:2334, 2009.

Rahul Banerjee et al., *J. Am. Chem. Soc.*, 131(11):3875, 2009.
Roswell and Yaghi, *J. Am. Chem. Soc.*, 128:304, 2006.
Sorrell, In: *Organic Chemistry*, -2$^{nd}$ Ed., University Science Books, 469, 2006.
Spek, *J. Appl. Crystallogr.*, 36:7-13, 2003.
Tanaka et al., *Chem. Commun.*, 3142, 2007.
Xiang et al., *Angew. Chem. Int. Ed.*, 49:4615, 2010.

What is claimed is:

1. A metal-organic framework (MOF) comprising a repeat unit of the formula $Zn_4(OH)_2(1,2,4-BTC)_2$, wherein 1,2,4-BTC is benzene-1,2,4-tricarboxylate.

2. The MOF of claim 1, further comprising one or more than one type of guest molecule.

3. The MOF of claim 2, wherein the guest molecule is a solvent molecule.

4. The MOF of claim 3, wherein the solvent molecule is water, N,N'-diethylformamide or N,N'-dimethylformamide.

5. The MOF of claim 2, wherein the guest molecule is a gas molecule.

6. The MOF of claim 5, wherein the gas molecule is $H_2$, $N_2$, Ar, $O_2$, $CO_2$, NO, $NO_2$ or CO.

7. The MOF of claim 5, wherein the guest molecule is an alkane$_{(C1-6)}$, alkene$_{(C2-4)}$, alkyne$_{(C2-6)}$, alcohol$_{(C1-6)}$, arene$_{(C6-8)}$ or a substituted version of any of these.

8. The MOF of claim 7, wherein the alkane$_{(C1-6)}$ is $CH_4$, $C_2H_6$, $C_3H_8$, $C_4H_{10}$, $C_5H_{12}$ or $C_6H_{14}$.

9. The MOF of claim 7, wherein the alkane$_{(C1-6)}$ is a cycloalkane$_{(C3-6)}$ selected from the group consisting of $C_3H_6$, $C_4H_8$, $C_5H_{10}$ and $C_6H_{12}$.

10. The MOF of claim 7, wherein the alkene$_{(C2-6)}$ is $C_2H_4$, $C_3H_6$, $C_4H_8$, $C_5H_{10}$ or $C_6H_{12}$.

11. The MOF of claim 7, wherein the alkyne$_{(C2-6)}$ is $C_2H_2$.

12. The MOF of claim 7, wherein the alcohol$_{(C1-6)}$ is methanol, ethanol, n-propanol, isopropanol, n-butanol or isobutanol.

13. The MOF of claim 7, wherein the guest molecule is an arene$_{(C6-8)}$ or a substituted arene$_{(C6-8)}$.

14. The MOF of claim 13, wherein the substituted arene$_{(C6-8)}$ is nitrobenzene, 1,2-dinitrobenzene, 1,3-dinitrobenzene, 1,4-dinitrobenzene, 1,2,4-trinitrobenzene or 1,3,5-trinitrobenzene.

15. The MOF of claim 1, substantially free from any solvent molecules.

16. The MOF of claim 1, having a weight percentage at least 90% attributable to repeat units of the formula $Zn_4(OH)_2(1,2,4-BTC)_2$.

17. The MOF of claim 1, having a weight percentage at least 95% attributable to repeat units of the formula $Zn_4(OH)_2(1,2,4-BTC)_2$.

18. The MOF of claim 1, having a weight percentage at least 99% attributable to repeat units of the formula $Zn_4(OH)_2(1,2,4-BTC)_2$.

19. A method of storing a compound within a metal-organic framework (MOF) comprising:
   (a) obtaining MOF comprising a repeat unit of the formula $Zn_4(OH)_2(1,2,4-BTC)_2$, wherein 1,2,4-BTC is benzene-1,2,4-tricarboxylate; and
   (b) combining the MOF with a first compound such that the first compound is stored within the MOF.

20. A method of detecting a compound using an MOF comprising:
   (a) obtaining a MOF comprising a repeat unit of the formula $Zn_4(OH)_2(1,2,4-BTC)_2$, wherein 1,2,4-BTC is benzene-1,2,4-tricarboxylate;
   (b) combining the MOF with a first compound such that the first compound enters the MOF to form an MOF•guest complex; and
   (c) comparing the luminescence intensity of the MOF with the luminescence intensity of the MOF•guest complex so as to detect the first compound.

21. A method of separating two or more compounds using an MOF comprising:
   (a) obtaining a metal-organic framework (MOF) comprising a repeat unit of the formula $Zn_4(OH)_2(1,2,4-BTC)_2$, wherein 1,2,4-BTC is benzene-1,2,4-tricarboxylate;
   (b) combining the MOF with a mixture comprising a first compound and a second compounds; and
   (c) separating the two or more compounds based on their differential diffusion rate within the MOF.

* * * * *